(12) United States Patent
Manoux et al.

(10) Patent No.: US 8,662,369 B1
(45) Date of Patent: Mar. 4, 2014

(54) BARBED SURGICAL STAPLE

(75) Inventors: Philipe R. Manoux, Oakland, CA (US);
Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 107 days.

(21) Appl. No.: 12/788,911

(22) Filed: May 27, 2010

(51) Int. Cl.
*A61B 17/068* (2006.01)

(52) U.S. Cl.
USPC .............. 227/175.1; 227/180.1; 606/153

(58) Field of Classification Search
USPC ........ 227/175.1; 606/142, 153, 221, 151, 213
See application file for complete search history.

(56) References Cited

U.S. PATENT DOCUMENTS

| | | | |
|---|---|---|---|
| 3,581,551 | A | 6/1971 | Wilkinson |
| 3,650,453 | A | 3/1972 | Smith, Jr. |
| 3,675,688 | A | 7/1972 | Bryan et al. |
| 3,899,914 | A | 8/1975 | Akiyama |
| 3,955,581 | A | 5/1976 | Spasiano et al. |
| 4,086,926 | A | 5/1978 | Green et al. |
| 4,228,895 | A | 10/1980 | Larkin |
| 4,275,813 | A | 6/1981 | Noiles et al. |
| 4,475,679 | A | 10/1984 | Fleury, Jr. |
| 4,589,416 | A | 5/1986 | Green |
| 4,633,861 | A | 1/1987 | Chow et al. |
| 4,655,222 | A | 4/1987 | Florez et al. |
| 4,719,917 | A | 1/1988 | Barrows et al. |
| 4,762,260 | A | 8/1988 | Richards et al. |
| 4,969,591 | A | 11/1990 | Richards et al. |
| 4,978,049 | A | 12/1990 | Green |
| 5,156,315 | A | 10/1992 | Green et al. |
| 5,170,925 | A | 12/1992 | Madden et al. |
| 5,192,288 | A | 3/1993 | Thompson et al. |
| 5,307,976 | A | 5/1994 | Olson et al. |
| 5,413,272 | A | 5/1995 | Green et al. |
| 5,476,206 | A | 12/1995 | Green |
| 5,547,117 | A | 8/1996 | Hamblin et al. |
| 5,553,765 | A | 9/1996 | Knodel et al. |
| 5,620,289 | A | 4/1997 | Curry |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

Gong, Shao W., "Perfectly flexible mechanism and integrated mechanism system design", *Mechanism and Machine Theory 39* (2004), (Nov. 2004), 1155-1174.

(Continued)

*Primary Examiner* — Thanh K Truong
*Assistant Examiner* — Nathaniel Chukwurah
(74) *Attorney, Agent, or Firm* — Cardica, Inc.

(57) ABSTRACT

An exemplary surgical staple may include a base including a first end and a second end; a single tine extending from the second end of the base; and a barb extending from the base at a location between the first end of the base and the second end of the base. An end of such a staple may be frangibly affixed to a feeder belt. Another exemplary surgical apparatus may include at least one staple including a base including a first end and a second end, a first tine extending from the second end of the base, and a second tine extending from the base at a location between the first end of the base and the second end of the base.

5 Claims, 6 Drawing Sheets

(56) References Cited

U.S. PATENT DOCUMENTS

| | | | |
|---|---|---|---|
| 5,630,541 A | 5/1997 | Williamson, IV et al. | |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,843,084 A * | 12/1998 | Hart et al. | 606/77 |
| 5,855,311 A | 1/1999 | Hamblin et al. | |
| 5,871,135 A | 2/1999 | Williamson, IV et al. | |
| 5,875,538 A | 3/1999 | Kish et al. | |
| 5,894,979 A | 4/1999 | Powell | |
| 5,918,791 A | 7/1999 | Sorrentino et al. | |
| 5,964,774 A | 10/1999 | McKean et al. | |
| 6,254,615 B1 * | 7/2001 | Bolduc et al. | 606/142 |
| 6,306,149 B1 | 10/2001 | Meade | |
| 6,391,038 B2 | 5/2002 | Vargas et al. | |
| 6,419,682 B1 | 7/2002 | Appleby et al. | |
| 6,592,597 B2 | 7/2003 | Grant et al. | |
| 6,602,252 B2 | 8/2003 | Mollenauer | |
| 6,716,232 B1 | 4/2004 | Vidal et al. | |
| 6,817,508 B1 | 11/2004 | Racenet | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,111,768 B2 | 9/2006 | Cummins et al. | |
| 7,128,253 B2 | 10/2006 | Mastri et al. | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,258,262 B2 | 8/2007 | Mastri et al. | |
| 7,401,720 B1 | 7/2008 | Durrani | |
| 7,434,715 B2 | 10/2008 | Shelton, IV et al. | |
| 7,467,740 B2 | 12/2008 | Shelton, IV et al. | |
| 7,497,865 B2 | 3/2009 | Willis et al. | |
| 7,506,791 B2 | 3/2009 | Omaits et al. | |
| 7,517,356 B2 | 4/2009 | Heinrich | |
| 7,588,177 B2 | 9/2009 | Racenet | |
| 7,604,151 B2 | 10/2009 | Hess et al. | |
| 7,635,073 B2 | 12/2009 | Heinrich | |
| 7,635,373 B2 | 12/2009 | Ortiz | |
| 7,641,432 B2 | 1/2010 | Lat et al. | |
| 7,644,848 B2 | 1/2010 | Swayze et al. | |
| 2003/0120284 A1 | 6/2003 | Palacios et al. | |
| 2003/0236551 A1 | 12/2003 | Peterson | |
| 2005/0055087 A1 * | 3/2005 | Starksen | 623/2.11 |
| 2005/0154406 A1 * | 7/2005 | Bombard et al. | 606/153 |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2006/0253143 A1 | 11/2006 | Edoga et al. | |
| 2006/0278679 A1 * | 12/2006 | Viola et al. | 227/155 |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2008/0078807 A1 | 4/2008 | Hess et al. | |
| 2008/0272175 A1 | 11/2008 | Holsten et al. | |
| 2009/0065552 A1 * | 3/2009 | Knodel et al. | 227/180.1 |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, Feb. 21, 2001.

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", J. Endourology 18(9), (Nov. 2004),811-817.

Steichen, Felicien M., et al., "Mechanical Sutures in Surgery", *Brit. J. Surg.* 60(3), (Mar. 1973),191-197.

"Notification of Transmittal of the International Search Report and the Written Opinion of the International Searching Authority", PCT/US2008/075449.

"International Search Report", PCT/US2008/075449.

"Written Opinion of the International Searching Authority", PCT/US2008/075449.

"Cardica Microcutter Implant Delivery Device 510(k), Cover Sheet, Table 10.1, "Substantial Equivalence Comparison," and Section 12, "Substantial Equivalence Discussion"".

\* cited by examiner

BARBED SURGICAL STAPLE

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter.

In order to overcome these difficulties, Cardica, Inc. of Redwood City, Calif. has developed a true multi-fire endocutter that is capable of firing multiple times without the need to utilize single-use-cartridges. Such an endocutter is described in, for example, U.S. Patent Application Publication No. 2009/0065552, published on Mar. 12, 2009 (the "Endocutter Publication"), which is hereby incorporated by reference herein in its entirety.

BRIEF DESCRIPTION OF THE DRAWINGS

The use of the same reference symbols in different figures indicates similar or identical items.

DETAILED DESCRIPTION

Figure 1:
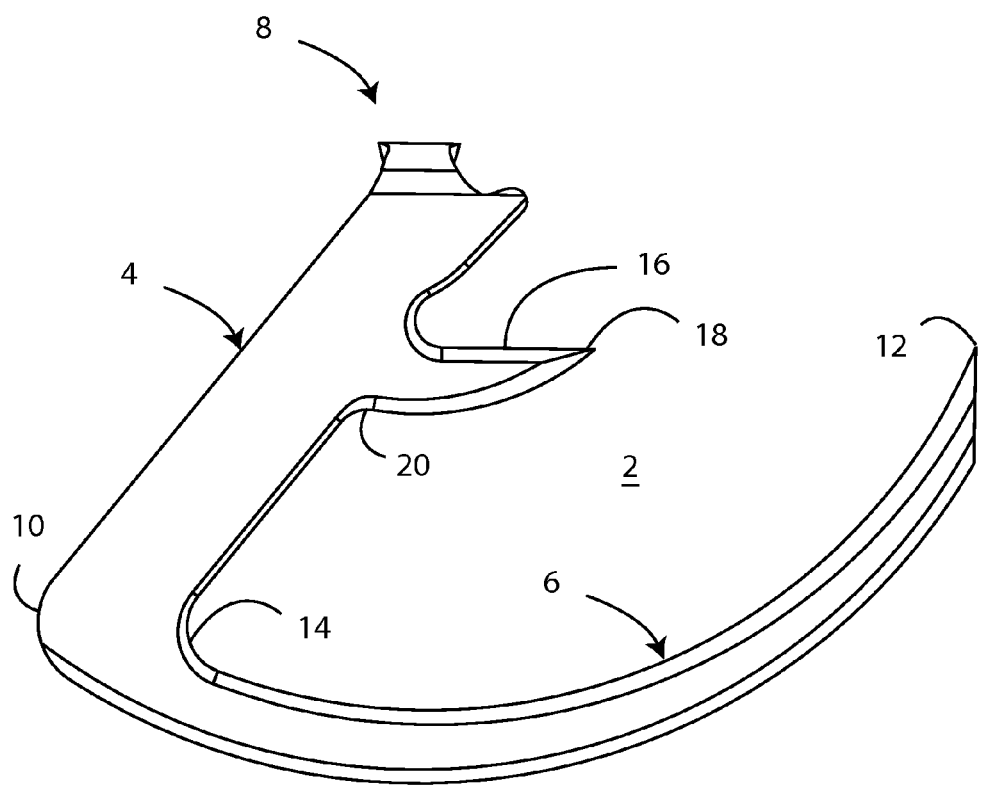
FIG. 1 is a side view of a barbed surgical staple in an open state.

Referring to FIG. 1, an exemplary surgical staple 2 may include a base 4 and a single tine 6 extending from an end of the base 4. The base 4 may have a first end 8 and a second end 10, and the tine 6 may extend from the second end 10 of the base 4. Alternately, the tine 6 may extend from a location near an end of the base 4, or from a different location on the base 4 entirely. The surgical staple 2 may be independent of other staples or carriers, or may be frangibly affixed to a feeder belt in the same manner as set forth in the Endocutter Publication. If so, the first end 8 of the base 4 may be frangibly attached to the feeder belt, and the second end 10 of the base may be connected to the tine 6. Advantageously, the surgical staple 2 is fabricated from a single piece of material, such as stainless steel. However, the surgical staple 2 may be fabricated from multiple independent components that are connected together in any suitable manner. The tine 6 may include a free end 12, and an opposite end 14 that is connected to the second end 10 of the base 4. The free end 12 of the tine 6 may be sharpened to facilitate entry into tissue. However, the tine 6 may be small enough in cross-section and size that its free end need not be sharpened in order to penetrate tissue. The tine 6 may be curved in a direction both outward from the base 4 and toward the first end 8 of the base 4, as shown in FIG. 1, such that the free end 12 of the tine 6 may be spaced apart from the first end 8 of the base 4 but positioned longitudinally at a location substantially the same as the first end 8 of the base 4. As used in the description of the staple 2, without limitation as to the orientation of the staple 2 in used, the "longitudinal" direction refers to the direction along which the base 4 extends. If the base 4 is curved, the longitudinal direction refers to the direction along a straight line that connects the ends 8, 10 of the base 4.

A barb 16 may extend from the base 4 at a location between its ends 8, 10. The barb 16 has a free end 18 and an opposite end 20 that is connected to the base 4. The free end 18 of the barb 16 may be sharpened to facilitate entry into tissue. However, the barb 16 may be small enough in cross-section and size that its free end need not be sharpened in order to penetrate tissue. The barb 16 is shorter in length than the tine 6. As a result, it is more resistant to deformation. The length of the barb 16 may be selected to minimize or prevent deflection of the barb 16 during deployment of the staple 2, as described in greater detail below. The barb 16 may be curved in a similar manner as the tine 6, in a direction outward from the base 4 and toward the first end 8 of the base 4, as shown in FIG. 1.

Figure 2:
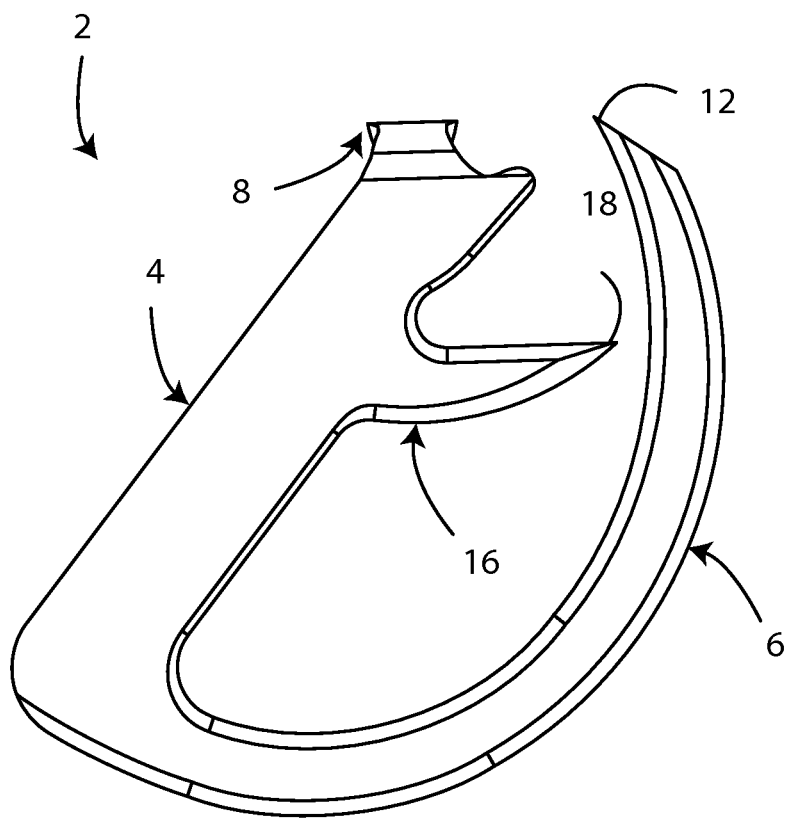
FIG. 2 is a side view of the staple of FIG. 1 in a closed state.
Figure 3:
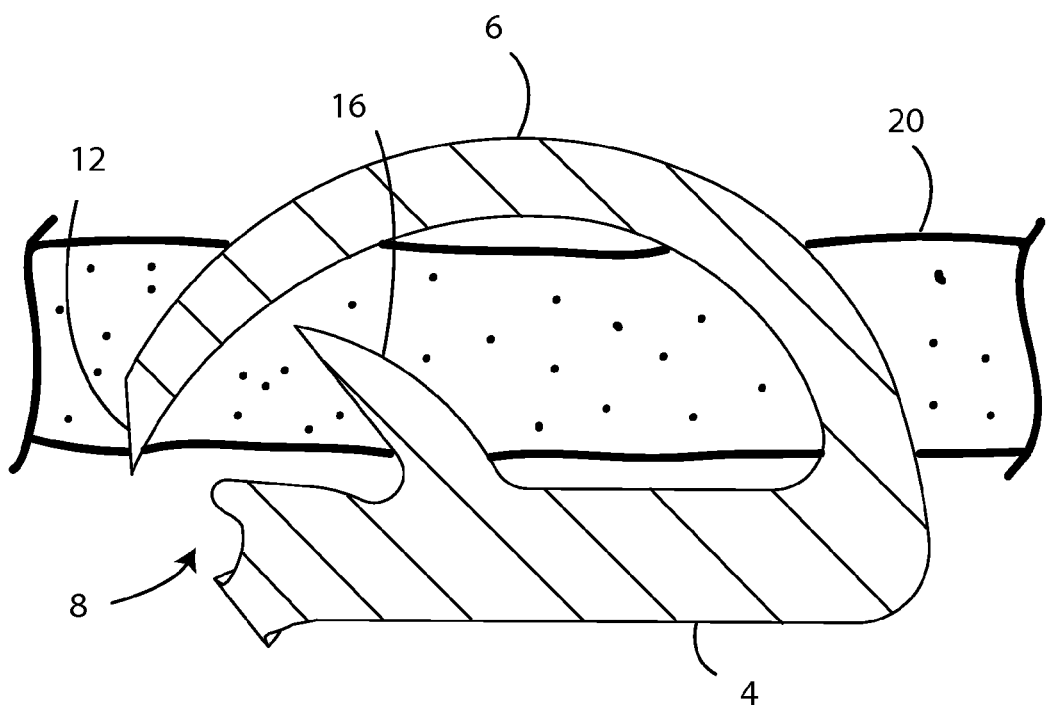
FIG. 3 is a side cross-section view of the closed staple of FIG. 2 in tissue.

Referring also to FIG. 2, the staple 2 is shown in a closed state. Deployment and closure of the staple 2 may be performed substantially as set forth in the Endocutter Publication. To summarize, a wedge may contact the staple directly, urge the tine 6 against an anvil, and cause the free end 12 of the tine 6 to bend toward the first end 8 of the base 4. At the same time, the staple 2 as a whole is rotated about the junction between the first end 8 of the base 4 and the feeder belt to which the first end 8 of the base 4 is affixed. This rotation breaks the staple 2 from the feeder belt after the staple 2 has closed. In the closed state, the free end 12 of the tine 6 is closer to the base 4 than in the open state. As shown in FIG. 2, the free end 12 of the tine 6 may contact the base 4 in the closed state, but the free end 12 of the tine 6 need not contact the base 4 when the staple 2 is closed. In the closed state, the free end 18 of the barb 16 may be closer to the tine 6 than in the open state. The free end 18 of the barb 16 may contact the tine 6 in the closed state, but need not do so. Contact between the free end 18 of the barb 16 and the tine 6 may cause deformation of the barb 16. Alternately, the barb 16 is stiff enough, and/or the staple 2 is closed in such a manner, that the barb 16 substantially does not deform in the closed state. Referring also to FIG. 3, in the closed state, the staple 2 traps tissue 20 between the base 4 and the tine 6. The base 4 is positioned on one side of tissue 20; the tine 6 may extend through that layer of tissue 20 to its other side, then back into that layer of tissue 20 to come into proximity to the base 4. The barb 16 may extend into but not completely through the layer of tissue 20, contacting the tine 6 or coming into proximity to the tine 6 in order to better trap and hold tissue 20 between the tine 6 and the base 4 when the staple 2 is in the closed state.

Figure 4:
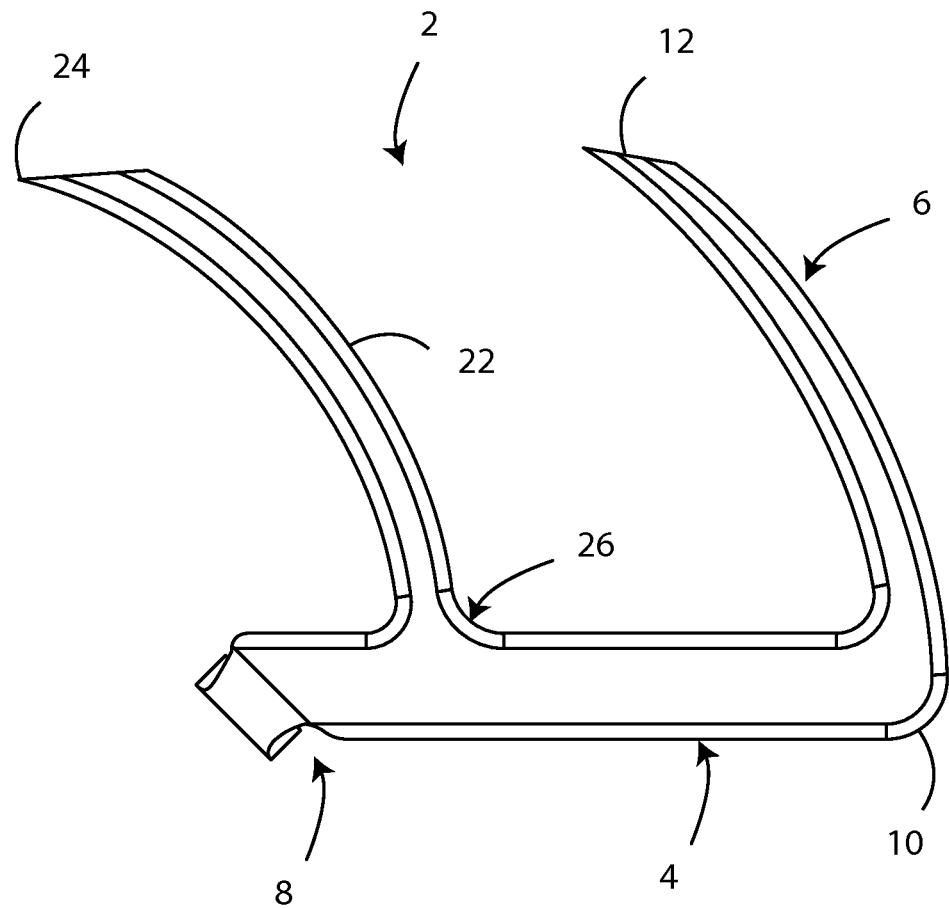
FIG. 4 is a side view of another embodiment of a surgical staple in an open state.

Referring to FIG. 4, another example of a surgical staple 2 is shown. The base 4 and the tine 6 of this staple 2 are substantially as set forth with respect to FIGS. 1-3 above. Instead of a barb 16, a second tine 22 extends from the base 4 between the tine 6 and the first end 8 of the base 4. The second tine 22 is longer than the barb 16 and shorter than, or substantially the same length as, the tine 6. Alternately, the second tine 22 may be longer than the tine 6. The second tine 22 may have a free end 24 and an opposite end 26 that is connected to the base 4. The free end 24 of the second tine 22 may be sharpened to facilitate entry into tissue. However, the second tine 22 may be small enough in cross-section and size that its free end need not be sharpened in order to penetrate tissue. The second tine 22 may be curved in a direction both outward from the base 4 and toward the first end 8 of the base 4, as shown in FIG. 4, such that the free end 24 of the second tine 22 may be spaced apart from the first end 8 of the base 4 but positioned longitudinally at a location substantially the same as the first end 8 of the base 4. The tine 6 may be curved in a direction both outward from the base 4 and toward the first end 8 of the base 4, as shown in FIG. 4, such that the free end 12 of the tine 6 may be spaced apart from the first end 8 of the base 4 but positioned longitudinally between the free end 24 of the second tine 24 and the second end 10 of the tine 6. Both the tine 6 and second tine 22 may possess substantially the same degree and shape of curvature. However, the tine 6 and second tine 22 need not be curved in the same manner.

Figure 5:
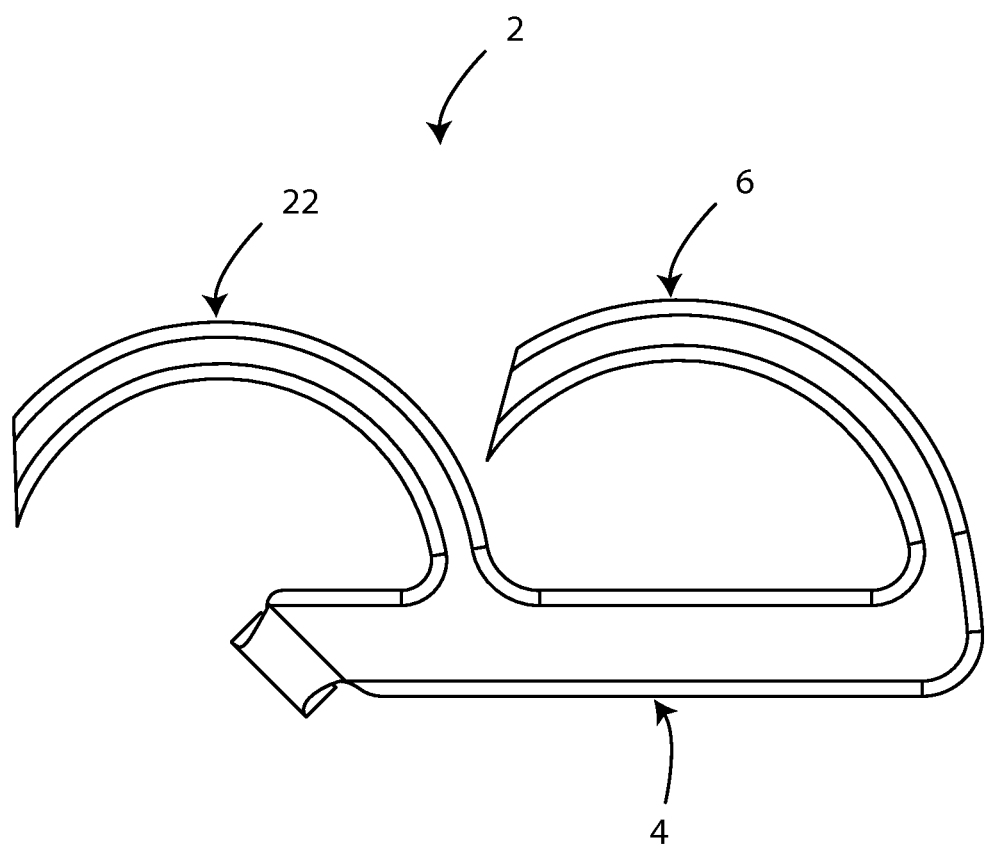
FIG. 5 is a side view of the staple of FIG. 4 in a closed state.

Referring also to FIG. 5, the staple of FIG. 4 may be closed by urging the tine 6 and second tine 22 into a staple pocket in an anvil, as set forth in the Endocutter Publication. Due to the curvature of the tines 6, 22, they close in the same direction, rather than in opposite directions. As a result, a substantially "B-shaped" configuration of the closed staple 2 may result, where one-half of the B is oriented in the opposite direction from that of a conventional surgical staple. The tines 6, 22 of the staple 2 of FIG. 5 are sized and shaped such that they do not substantially interfere with one another.

Figure 6:
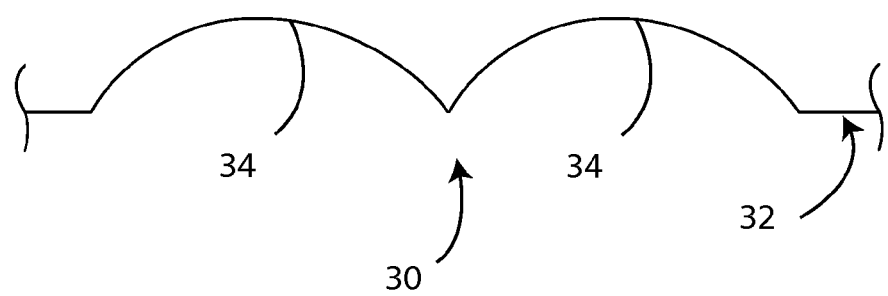
FIG. 6 is a side view of an exemplary anvil pocket usable with the staple of FIG. 4, as viewed along line A-A of FIG. 7.
Figure 7:
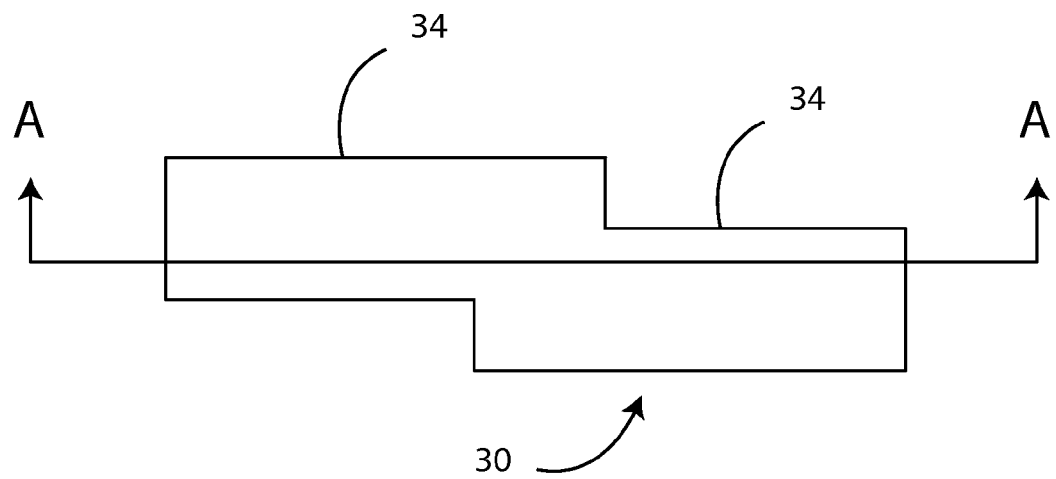
FIG. 7 is a top view of the exemplary anvil pocket of FIG. 6.

Alternately, the tines 6, 22 may be sized, shaped and/or otherwise configured to contact one another during closure, such as to provide added deformation of one or more tines 6, 22. Alternately, the tine 6 may be laterally offset from the second tine 22 to prevent contact between the two. Referring to FIGS. 6-7, a staple pocket 30 may be defined in an anvil 32, where each staple pocket 30 corresponds to a single staple 2. Each staple pocket 30 may include two sub-pockets 34, each corresponding to a different tine 6, 22 of the staple 2. Engagement between each tine 6, 22 and its corresponding sub-pocket 34 deforms the tines 6, 22 to close in the same direction. The tines 6, 22 may be laterally offset from one another, such that the sub-pockets 34 are laterally offset from one another as seen in FIG. 7. In this way, the tines 6, 22 can close without interference with one another, in the event that the tine 6 is long enough to close onto the second tine 22 if the tines 6, 22 were not offset.

While the invention has been described in detail, it will be apparent to one skilled in the art that various changes and modifications can be made and equivalents employed, without departing from the present invention. It is to be understood that the invention is not limited to the details of construction, the arrangements of components, and/or the steps of performing anastomosis set forth in the above description or illustrated in the drawings. Therefore, the invention is not to be restricted or limited except in accordance with the following claims and their legal equivalents.

What is claimed is:

1. A surgical staple, comprising:
   a base including a first end configured for frangible attachment to a feeder belt and a second end;
   a single tine extending from said second end of said base to a sharpened free end, wherein said tine is curved both in a direction outward from said base and toward said first end of said base; and
   a barb extending from said base at a location between said first end of said base and said second end of said base, wherein said barb is substantially shorter than said tine and includes a sharpened free end.

2. The surgical staple of claim 1, wherein said barb is curved both in a direction outward from said base and toward said first end of said base.

3. The surgical staple of claim 1, wherein said tine is deformable from an open state in which said free end of said tine is spaced apart from said base to a closed state in which said free end of said tine contacts said base.

4. The surgical staple of claim 3, wherein said tine contacts said barb in said closed state.

5. The surgical staple of claim 4, wherein contact between said tine and said barb causes said barb to deform.

* * * * *